(12) United States Patent
Poland

(10) Patent No.: US 11,553,895 B2
(45) Date of Patent: Jan. 17, 2023

(54) ULTRASOUND SYSTEM WITH PROCESSOR DONGLE

(71) Applicant: KONINKLIJKE PHILIPS N.V., Eindhoven (NL)

(72) Inventor: McKee Dunn Poland, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1080 days.

(21) Appl. No.: 15/745,227

(22) PCT Filed: Jul. 1, 2016

(86) PCT No.: PCT/IB2016/053956
§ 371 (c)(1),
(2) Date: Jan. 16, 2018

(87) PCT Pub. No.: WO2017/013511
PCT Pub. Date: Jan. 26, 2017

(65) Prior Publication Data
US 2018/0220993 A1 Aug. 9, 2018

Related U.S. Application Data

(60) Provisional application No. 62/194,907, filed on Jul. 21, 2015.

(51) Int. Cl.
*A61B 8/00* (2006.01)
*G01S 7/52* (2006.01)

(52) U.S. Cl.
CPC .......... *A61B 8/4411* (2013.01); *A61B 8/4427* (2013.01); *A61B 8/4472* (2013.01);
(Continued)

(58) Field of Classification Search
None
See application file for complete search history.

(56) References Cited

U.S. PATENT DOCUMENTS

| 5,229,933 A | 7/1993 | Larson, III |
| 5,690,114 A | 11/1997 | Chiang |

(Continued)

FOREIGN PATENT DOCUMENTS

| JP | 2012176056 A | 9/2012 |
| JP | 2014207990 A | 11/2014 |
| WO | 2017009735 A1 | 1/2017 |

*Primary Examiner* — Keith M Raymond
*Assistant Examiner* — Adam D. Kolkin

(57) ABSTRACT

A highly portable ultrasound system is configured using a wireless ultrasound probe (10), a processor dongle (30) containing a radio and a digital processor running an operating system and an ultrasound control program, and any conveniently available television receiver or display monitor. The sonographer only needs to carry the small wireless probe and the thumbdrive-like dongle in order to turn any available display device, together with the two components carried by the sonographer, into a completely functional ultrasound system. The sonographer can enter a patient's hospital room, plug the processor dongle into the patient monitor in the room, and conduct an ultrasound exam using the patient monitor as the system display, for instance. The system can be controlled by a touchscreen tablet computer, a wireless mouse, or by distinct gestures made by the probe.

12 Claims, 8 Drawing Sheets

(52) U.S. Cl.
CPC .............. *A61B 8/461* (2013.01); *A61B 8/467* (2013.01); *A61B 8/54* (2013.01); *A61B 8/56* (2013.01); *G01S 7/5208* (2013.01); *G01S 7/52082* (2013.01); *G01S 7/52084* (2013.01)

(56) References Cited

U.S. PATENT DOCUMENTS

| | | | |
|---|---|---|---|
| 5,997,479 | A | 12/1999 | Savord et al. |
| 6,142,946 | A | 11/2000 | Hwang et al. |
| 6,375,617 | B1 | 4/2002 | Fraser |
| 7,591,786 | B2 * | 9/2009 | Holmberg ................ A61B 8/00 600/437 |
| 2003/0139664 | A1 * | 7/2003 | Hunt ................... G01S 7/52023 600/407 |
| 2009/0318758 | A1 * | 12/2009 | Farr ..................... A61B 1/0655 600/112 |
| 2010/0160786 | A1 * | 6/2010 | Nordgren ............... A61B 8/467 600/459 |
| 2010/0168576 | A1 * | 7/2010 | Poland .................... A61B 8/00 600/443 |
| 2011/0156924 | A1 * | 6/2011 | Nadeem ................ G08G 1/0104 340/905 |
| 2013/0018263 | A1 | 1/2013 | Kimoto et al. |
| 2013/0065528 | A1 * | 3/2013 | Nagao ............... H04M 1/72527 455/41.2 |
| 2013/0197364 | A1 * | 8/2013 | Han ..................... A61B 8/5207 600/440 |
| 2014/0153796 | A1 * | 6/2014 | Sundaran ............... G16H 40/63 382/128 |
| 2015/0342561 | A1 * | 12/2015 | Takeda ............... A61B 17/3403 600/424 |
| 2015/0366540 | A1 * | 12/2015 | Sato ..................... A61B 8/5207 600/453 |
| 2016/0317131 | A1 * | 11/2016 | Schwartz Klessel .... A61B 8/54 |
| 2016/0331353 | A1 * | 11/2016 | Ralston ................ A61B 8/4444 |

* cited by examiner

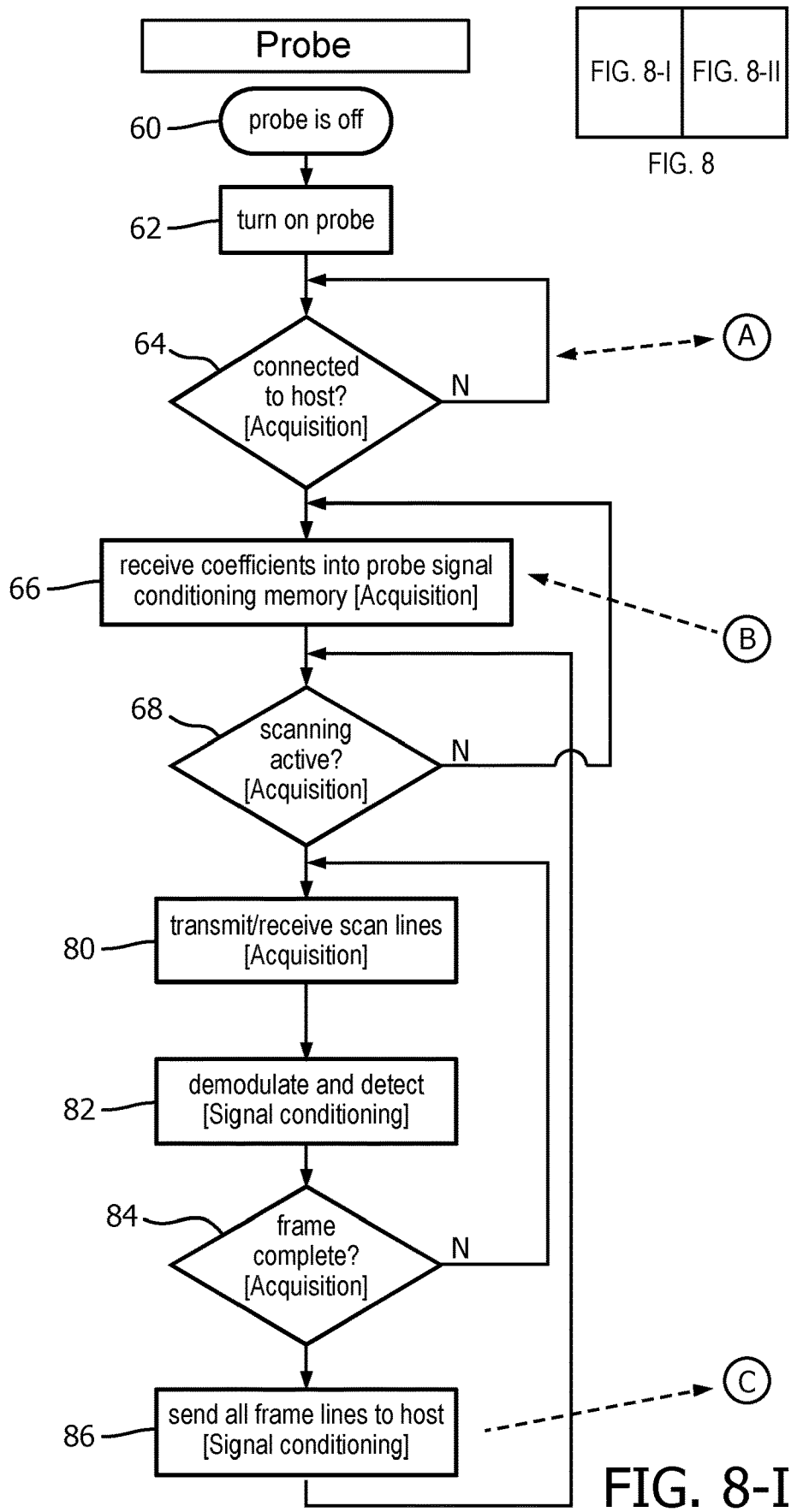
FIG. 8-I

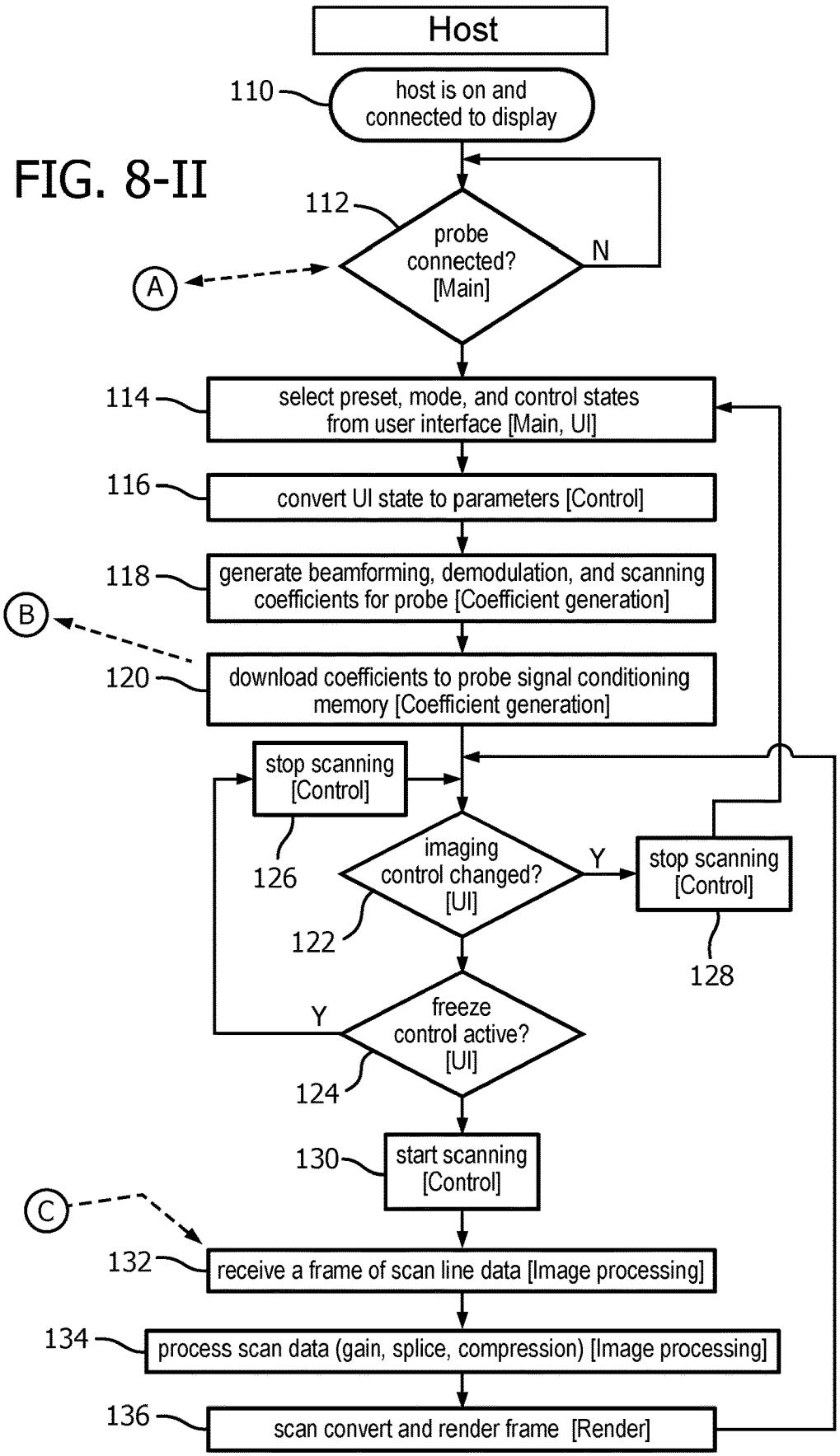
FIG. 8-II

ULTRASOUND SYSTEM WITH PROCESSOR DONGLE

This application is the U.S. National Phase application under 35 U.S.C. § 371 of International Application No. PCT/M2016/053956, filed on Jul. 1, 2016, which claims the benefit of Provisional Application Ser. No. 62/194,907, filed Jul. 21, 2015. These applications are hereby incorporated by reference herein.

This invention relates to medical diagnostic ultrasound systems and, in particular, to an ultrasound system using a processor in a thumbdrive-like "dongle."

Ultrasound system have become increasingly portable in recent years. The classic ultrasound system is cart-mounted with a control panel and display located above the electronics module. The cart-mounted system is easily positioned at the side of an exam table and the ultrasound probe plugs into the electronics module during use. About fifteen years ago system miniaturization started with desktop unit, then laptop-like configurations appeared. Today ultrasound systems are available in a tablet configuration with a USB probe containing the system electronics from the front end through image processing. The tablet serves as the image display device and touchscreen user interface. The Visiq ultrasound system, available from Philips Healthcare of Andover, Mass., USA, is an example of an ultrasound system in a tablet configuration. However, in all of these iterations in size the largest component has been the display screen, which has become the governing item in portability and miniaturization efforts. It has been technically possible to display live ultrasound images on a smartphone screen, but the small size generally prevents such images from being diagnostically useful. Thus, while laptop-like and tablet ultrasound systems are readily portable, the user must still carry a system with a display screen large enough to be diagnostically useful. It is desirable to advance these efforts in ultrasound system portability with a system configuration that eliminates the need to transport a diagnostically useful display screen.

In some aspects, the present invention includes an ultrasound system that can include a wireless ultrasound probe comprising a radio and configured to receive ultrasound probe control signals and send ultrasound image scan line data based on the control signals; a processor dongle having a digital processor configured to run an operating system and an ultrasound system control program and a radio, the dongle being configured to receive user interface commands for an imaging procedure, send ultrasound probe control signals to the ultrasound probe, receive image line data signals from the probe, and perform image processing of received image line data signals to generate an ultrasound image for display; and a television receiver or display monitor, coupled to the processor dongle and configured to display the ultrasound image generated by the dongle.

In certain aspects, the processor dongle can include an HDMI connector that is removably coupled to an HDMI port of the television receiver or display monitor. The radio can include an ultra-wideband (UWB) radio and the processor dongle further comprises an input port; and the system further comprises a UWB dongle plugged into the input port. In some aspects, the processor dongle can include a Wifi radio, the television receiver or display monitor can include a Wifi radio, and the television receiver or display monitor is coupled to the processor dongle using the Wifi radios. The system can also include an a.c. adapter configured to connect to and power the processor dongle when plugged into an a.c. outlet, and the processor dongle can include a port configured to connect a cable to the wireless probe for data transfer comprising the ultrasound, and the television receiver or display monitor can include a radio configured to couple to the processor dongle using the radio. The television receiver or display monitor can also include a patient monitor. In certain aspects, the system can include a tablet computer having a Wifi radio, the processor dongle radio can include a Wifi radio, and the tablet computer can display the ultrasound image generated by the dongle. In some aspects, the tablet computer can be configured to display user interface controls which are operated by a user to control the ultrasound system.

In some aspects, the present invention includes an ultrasound system including a wireless ultrasound probe comprising a radio configured to receive ultrasound probe control signals and send ultrasound image scan line data based on the control signals; a processor dongle having a digital processor configured to run an operating system and an ultrasound system control program and a radio, the dongle being configured to receive user interface commands for an imaging procedure, send ultrasound probe control signals to the ultrasound probe, receive image line data signals from the probe, and perform image processing of received image line data signals to generate an ultrasound image for display; a television receiver or display monitor, coupled to the processor dongle and configured to display the ultrasound image generated by the dongle; and a tablet computer having a radio configured to receive the ultrasound image generated by the processor dongle and display the ultrasound image in an ultrasound display, such that, in response to a user input, the system the processor dongle is further configured to display the ultrasound image on the television receiver or display monitor, the tablet computer, or both. The ultrasound display can further include a plurality of control buttons by which an ultrasound exam is controlled. And, the tablet computer can include a touchscreen display.

In certain aspects, the present invention includes an ultrasound system that includes an ultrasound probe having a probe cable configured to receive ultrasound probe control signals and send ultrasound image scan line data based on the control signals; a processor dongle having a port to which the probe cable is connected and a digital processor configured to run an operating system and an ultrasound system control program, the dongle being configured to receive user interface commands for an imaging procedure, send ultrasound probe control signals to the ultrasound probe, receive image line data signals from the probe, and perform image processing of received image line data signals to generate an ultrasound image for display; and a television receiver or display monitor, coupled to the processor dongle and configured to display the ultrasound image generated by the dongle.

The processor dongle can include a radio, the television receiver or display monitor can include a radio, and the television receiver or display monitor can be coupled to the processor dongle through the radios. The processor dongle can include a connector, the television receiver or display monitor can include a data port, and the processor dongle connector can be coupled to the data port. The ultrasound probe can include a motion sensor which generates signals in response to probe motion, and the processor dongle is configured to respond to signals generated in response to probe motion to control the operation of the ultrasound system.

Figure 6A:
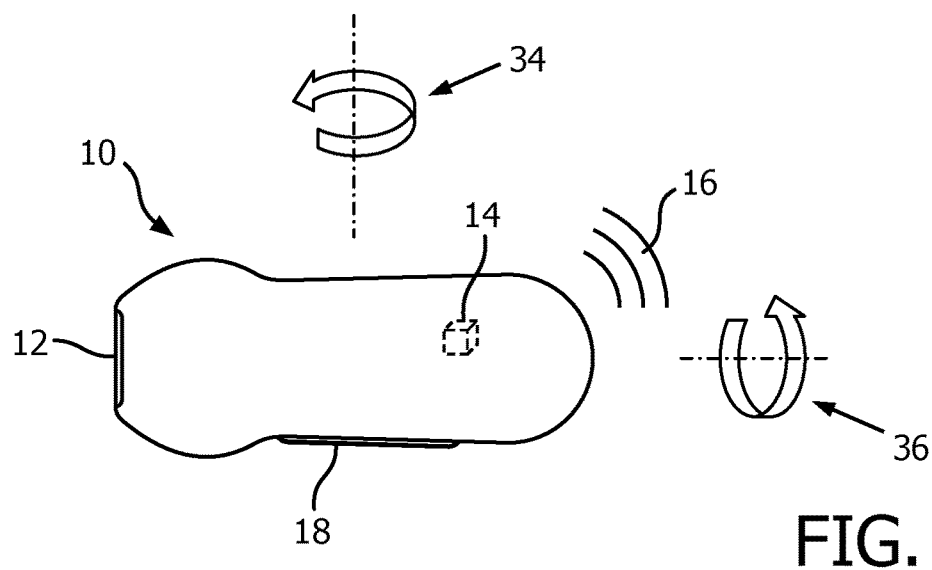
Figure 6B:
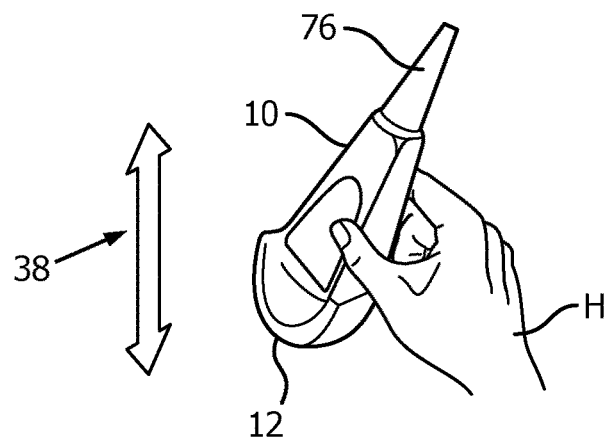
Figure 6C:
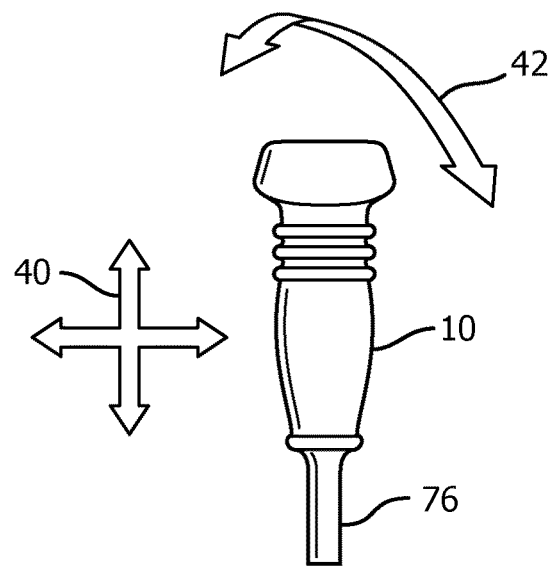

FIGS. 6a, 6b, and 6c illustrate the use of a wireless probe to control an ultrasound system by probe gestures.

Figure 7:
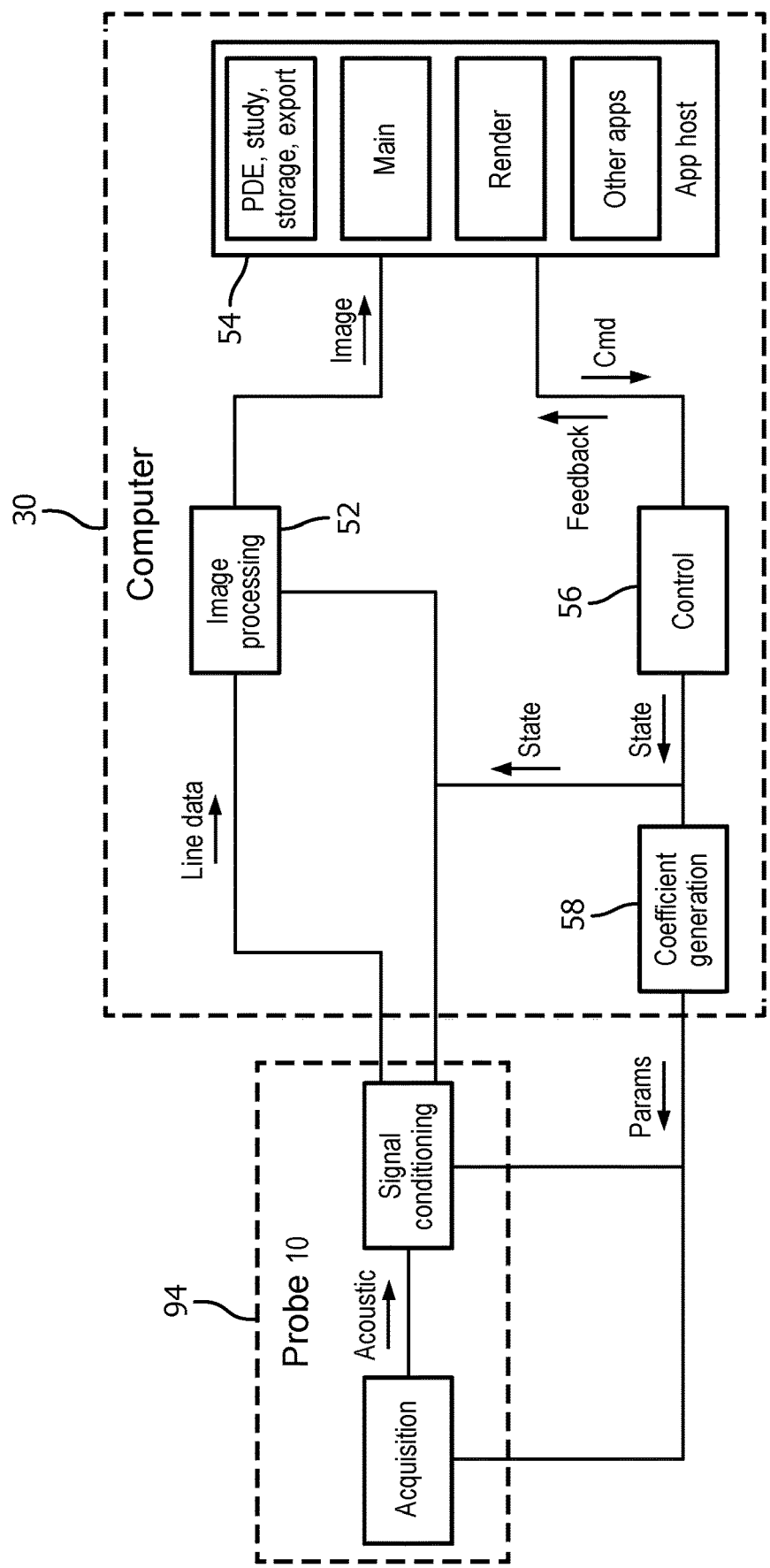

FIG. 7 is a functional block diagram of a probe and dongle processor operating as an ultrasound system in accordance with the principles of the present invention.

FIG. 8 is a flowchart illustrating the operation of the probe and dongle processor of FIG. 7 during the grayscale imaging mode.

In accordance with the principles of the present invention, an ultrasound system is configured with a thumbdrive-like "dongle" containing a processor running an ultrasound control program and a communication device. The communication device can operate wirelessly or wired or both, such as through a USB and/or HDMI connector, putting the dongle in communication with both an ultrasound probe and a display device which together comprise an ultrasound system. In one implementation described below the dongle plugs into a television receiver or display monitor which functions as the system display, and communicates wirelessly with the ultrasound probe. In another implementation the dongle plugs into a power source such as an a.c. USB plug or wall outlet to power the dongle, and communicates wirelessly with both the ultrasound probe and a display device. This configuration can, for example, use the ubiquitous patient monitor in a hospital room as the system display. The ultrasound system can thereby adapt virtually any available television receiver or display monitor to operate as the display for the ultrasound system.

Figure 1:
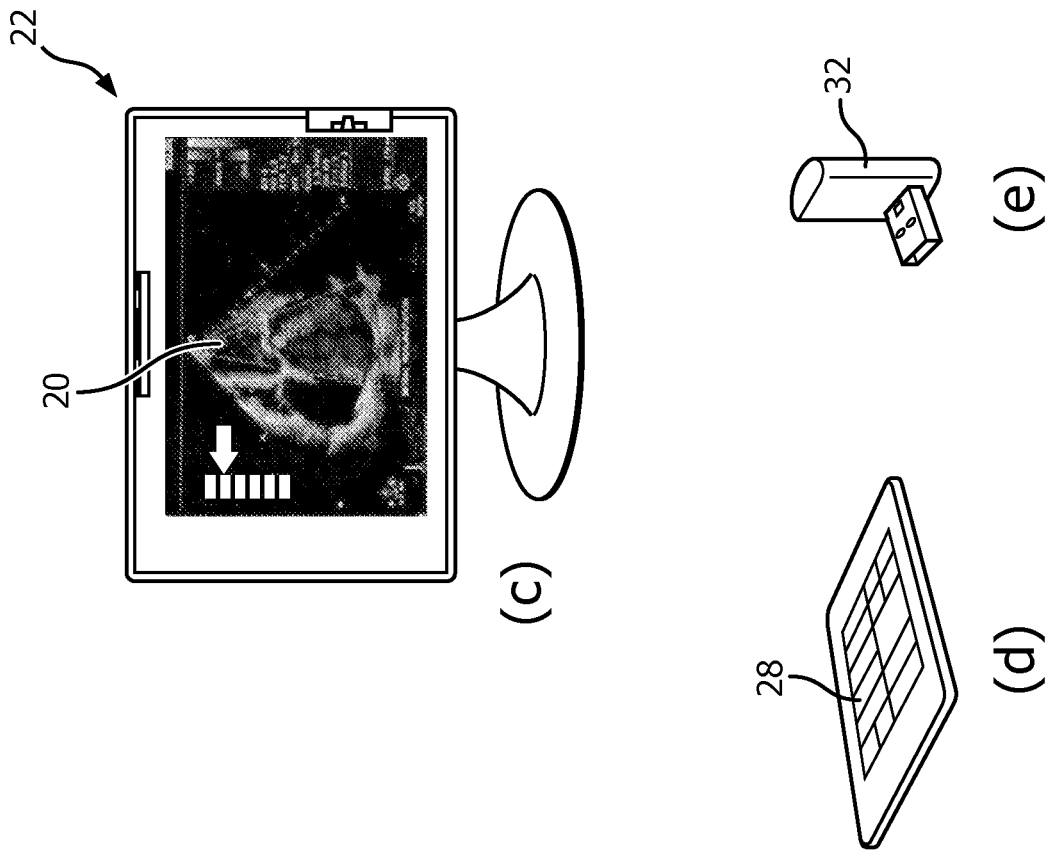
FIG. 1 illustrates a number of required and optional components of an ultrasound system of the present invention.

FIG. 1 illustrates a number of components which may be used to configure an ultrasound system in accordance with the principles of the present invention. FIG. 1(a) is a wireless ultrasound probe 10. The illustrated probe is formed by a USB probe 24, a unit with a transducer, front end electronics, signal and image processing in it and terminating at the back at a USB connector. The USB connector is not visible in this illustration because it is plugged into a radio power module 26, which provides wireless communication between the probe and other system components. FIG. 1(b) illustrates a dongle 30 containing a digital processor. The particular dongle shown is a compute stick commercially available from Intel Corporation of Santa Clara, Calif., USA. The Intel® compute stick is a thumbdrive-like dongle package with an HDMI connector 31 at one end and a USB port on the side. Inside is a digital quad-core Intel processor which runs the Windows® 8 operating system. The compute stick has digital audio capability, 2 GB of system memory, 32 GB of storage, and includes an HD graphics package and wireless communication by a Wifi (IEEE 802.11) radio and Bluetooth. When the compute stick 30 is plugged into an HDMI port of a television receiver or display monitor it can then use the receiver or monitor as the display device for Windows programs. A wireless keyboard and mouse can communicate with the compute stick processor and Windows operating system to turn the compute stick, keyboard, mouse and receiver or display into a computer system. In an implementation of the present invention a dongle such as the compute stick is used with an ultrasound probe such as that shown in FIG. 1(a) and a display such as display monitor 22 with a display screen 20 shown in FIG. 1(c) to form an ultrasonic diagnostic imaging system.

An ultrasound system configuration of the present invention may also include a tablet computer such as an iPad tablet computer 28, available from Apple Corp. of Cupertino, Calif., USA shown in FIG. 1(d). In implementations described below the tablet 28 performs various functions in the system, such as an auxiliary system display or a user interface. An ultrasound system of the present invention may also have further communication devices such as ultra wideband (UWB) radio dongle 32, such as the AL5350/AL5100UWB dongle chipset from Alereon of Austin, Tex. A UWB dongle with a USB connector such as the illustrated UWB dongle 32 can plug into the processor dongle 30, providing a configuration with numerous wireless communication connections including, in the case of the Intel compute stick, Wifi, Bluetooth, and UWB.

Figure 2:
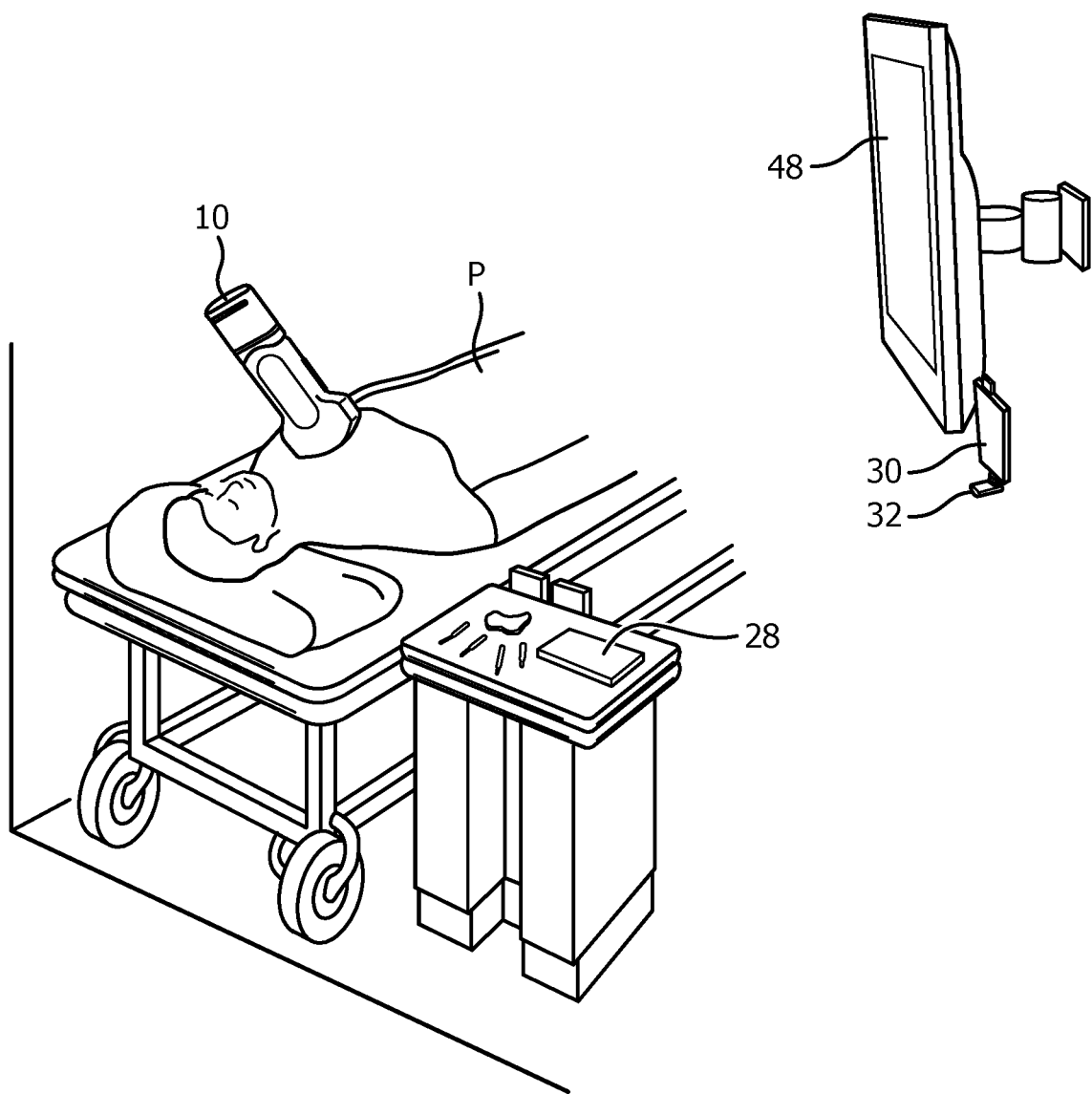
FIG. 2 illustrates a hospital room in which a patient monitor serves as the display for an ultrasound system of the present invention.

FIG. 2 illustrates a typical hospital room with a patient P. Mounted on the wall of the hospital room is a common patient monitor 48, which normally displays text and graphics of the vital signs of the patient P. In accordance with one implementation of the present invention, a processor dongle 30 is plugged into an auxiliary HDMI input of the patient monitor 48, allowing the patient monitor to select a display for an ultrasound system, preferably dedicating a portion of the display to ultrasound and another portion to vital signs. Plugged into the processor dongle 30 is a UWB dongle 32, which provides ultra wideband radio communication between the processor dongle 30 and wireless ultrasound probe 10 which is used to scan the patient. The images acquired by the probe 10 are processed and displayed by the dongle processor 30 on the screen of the patient monitor, providing the sonographer with a large, readily discernible ultrasound image.

This configuration further includes a tablet computer 28, shown on the bedside table next to the patient, which the sonographer can use as a user interface to control the functioning of the ultrasound system. The display on the tablet computer 28 is the same as is on the large wall monitor 48, including the user interface controls to set up and control the scanning procedure. The user can, however, pick up the tablet and by touching control buttons on the touchscreen of the tablet, operate the ultrasound system. To replicate the large display onto the tablet, an application called "Air Display," available from Avatron Software of Portland, Oreg., USA, may be utilized. With Air Display and its driver installed on the tablet computer and the dongle, the image that the dongle displays on the large monitor 48 is also replicated to the tablet display where its touch controls can be conveniently used.

Another option is to plug the processor dongle 30 into an a.c. adapter (e.g., a USB a.c. adapter) that is plugged into an a.c. outlet in the wall. This will continually power the processor dongle 30 and the dongle can communicate with both a display device and the probe wirelessly. For example, with the UWB dongle 32 plugged into the processor dongle 30, the wireless probe 10 can communicate with the dongle 30 over its UWB radio 26. The dongle 30 can then use its Wifi radio to communicate the display to a Wifi display device, such as a tablet computer 28 or a Wifi-capable television receiver or monitor 20. In some embodiments, the processor dongle can include a data port (e.g., a USB port) configured to connect a cable to the wireless probe. When coupled to the cable, the wireless probe can send data, including ultrasound image data, along the cable solely or in combination with the wireless transmission via the radio.

It is seen from the above examples that the ultrasound system components which are carried to the exam site include only the ultrasound probe 10 and the processor dongle 30, since the display component of the system is provided by any available television receiver or monitor at the site. This affords the utmost in portability, and the transported components can be carried in a handbag, pouch or pocket.

Further, if the processor dongle 30 and UWB dongle 32 are left installed at the exam site, then just the ultrasound probe 10 can be carried by the clinician. If multiple exam sites are equivalently configured with processor dongle 30 and UWB dongle 32, then ultrasound probe 10 is again the only transported component of the ultrasound system. Because the processor dongle 30 and UWB dongle 32 are relatively low cost components, only a low investment is required by the clinician or his organization, as compared to the normal outlay for a traditional cart based system.

Figure 3:
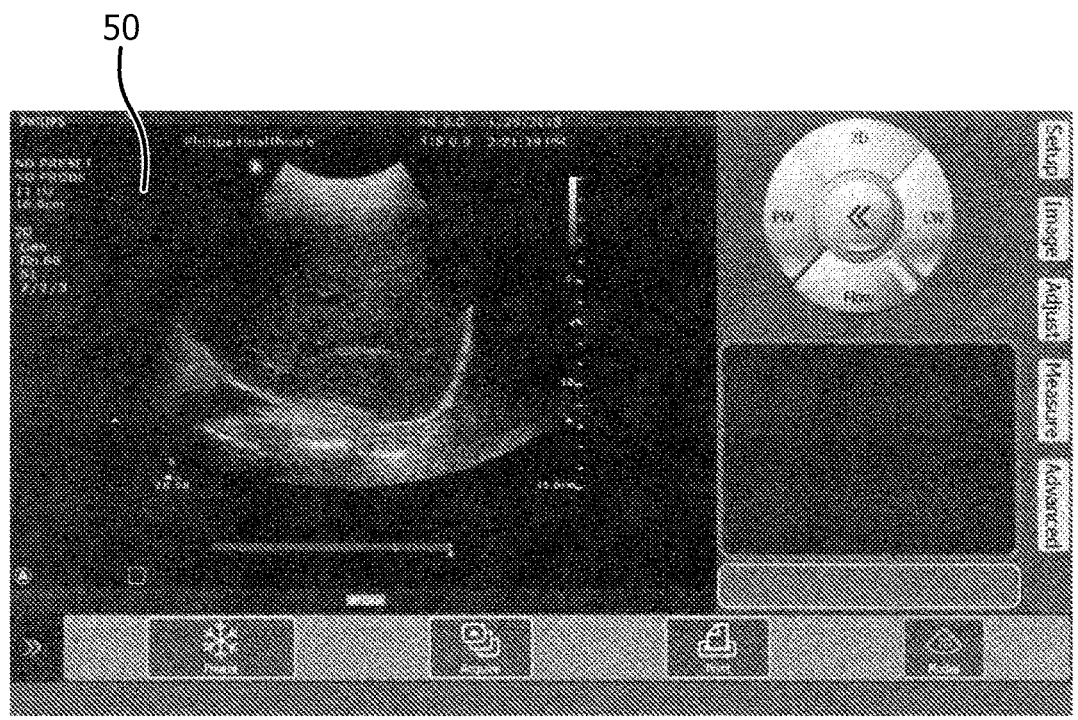
FIG. 3 illustrates a typical system display of an ultrasound system of the present invention.

FIG. 3 illustrates the ultrasound display 50 of a constructed implementation of the present invention which is shown on the receiver or monitor display and can also be shown on a tablet computer as described above. The ultrasound display 50 includes a live ultrasound image occupying most of the display, surrounded by the usual system and patient graphical information above and to the left of the image and a depth scale bar to the right of the image. The bar below the image contains a number of control buttons frequently used by a user during an ultrasound exam, including an image freeze button, a button to acquire and store a loop of images, a print button, and a mode button that toggles between imaging modes. There is also a large mode control to the right of the image, enabling the user to click directly to the 2D (grayscale) mode, the PW (spectral Doppler) mode, the CW (continuous wave Doppler) mode, or the Flow (color flow Doppler) mode. At the right side of the screen are a number of buttons used less frequently, including Setup, Image, Adjust, Measure, and Advanced control buttons.

Figure 4:
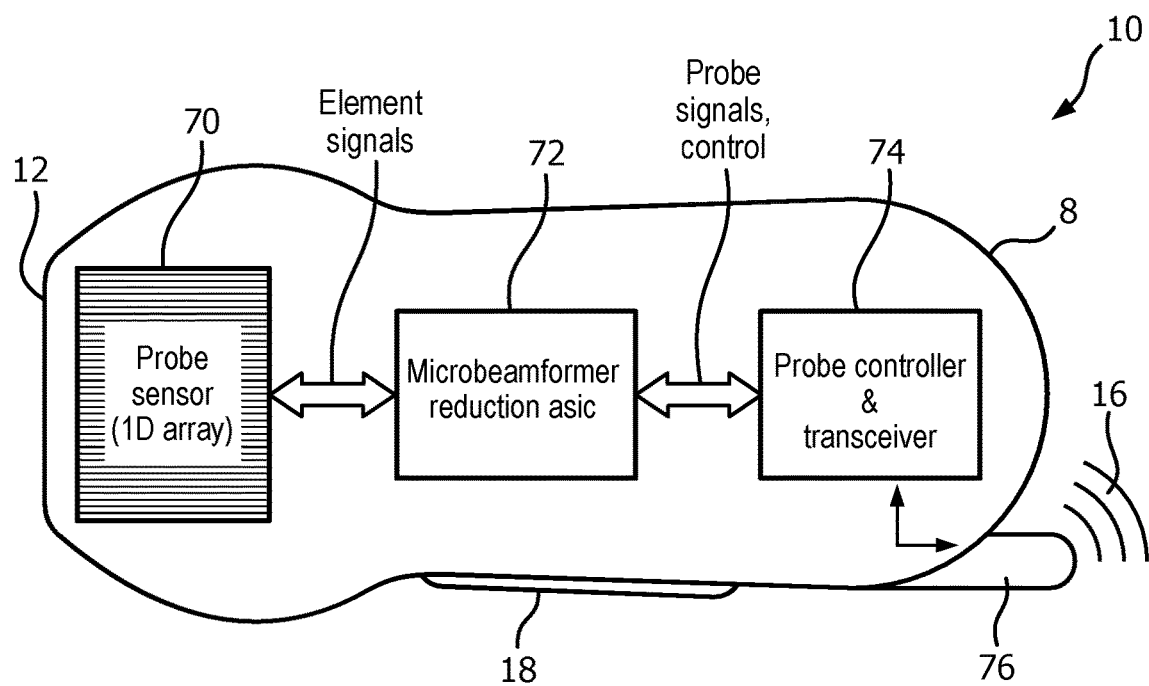
FIG. 4 illustrates in block diagram form a wireless ultrasound probe suitable for use as the ultrasound probe for an implementation of the present invention.

FIG. 4 illustrates the major functional components of a wireless ultrasound probe 10 suitable for use in an implementation of an ultrasound system of the present invention. In order to scan a two dimensional image plane the probe 10 uses a one-dimensional (1D) transducer array 70 located at the distal end 12 of the probe at the acoustic window of the probe. For both two dimensional and three dimensional electronic scan imaging, the probe will have a 2D matrix array transducer. The transducer array is formed of ceramic piezoelectric transducer elements, a piezoelectric polymer (PVDF), or may be a semiconductor-based micromachined ultrasound transducer (MUT) such as a PMUT (piezoelectric MUT) or a CMUT (capacitive MUT) array of elements. The array transducer 70 is driven by, and echoes are processed by, one or more microbeamformer ASICs 72. The microbeamformer 72 receives echo signals from the elements of the transducer array 70 and delays and combines the per-element echo signals into fully beamformed signals. For instance the microbeamformer 72 can receive echo signals from a row of 128 transducer elements of the array 70 and delay and combine these signals to form a fully beamformed signal as described in U.S. Pat. No. 6,142,946 (Hwang et al.) In a preferred embodiment fully beamformed and detected signals are produced by the probe for wireless transmission to the host ultrasound system, a processor dongle 30 running an application on the Windows operating system, which utilizes the reduced data rate of the detected signals to render acceptable real time imaging frame rates. Microbeamformer technology suitable for use in beamformer 72 is described in U.S. Pat. No. 5,229,933 (Larson III); U.S. Pat. No. 6,375,617 (Fraser); and U.S. Pat. No. 5,997,479 (Savord et al.) The beamformed echo signals are coupled to a probe controller and transceiver subsystem 74 which performs further signal processing as described below and transmits the beamformed signals as image scan lines to the host system. The host system then performs further image processing and displays the ultrasound images on a receiver or monitor 20. The probe controller and transceiver subsystem 74 also receives control signals from the host system as described below, and couples corresponding control signals to the microbeamformer 72 to, for example, steer and focus beams at a desired depth or transmit and receive signals of a desired mode (Doppler, B mode) to and from a desired location of an image region. Not shown in this illustration are the power subsystem and battery to power the probe, which are described below.

The transceiver of the probe controller and transceiver subsystem 74 transmits and receives r.f. signals 16 by means of an internal or stub antenna 76, similar to that of a cellphone. The stub antenna provides one of the same benefits as it does on a cellphone, which is that its small profile makes the probe convenient to hold and carry and reduces the possibility of damage to the antenna. Typically a ten meter range is sufficient for most exams, as the probe and dongle host are in close proximity to each other. Communication frequencies employed can be in the 4 GHz range, and suitable polymers for the probe case 8 such as ABS are relatively transparent to r.f. signals at these frequencies.

Figure 5:
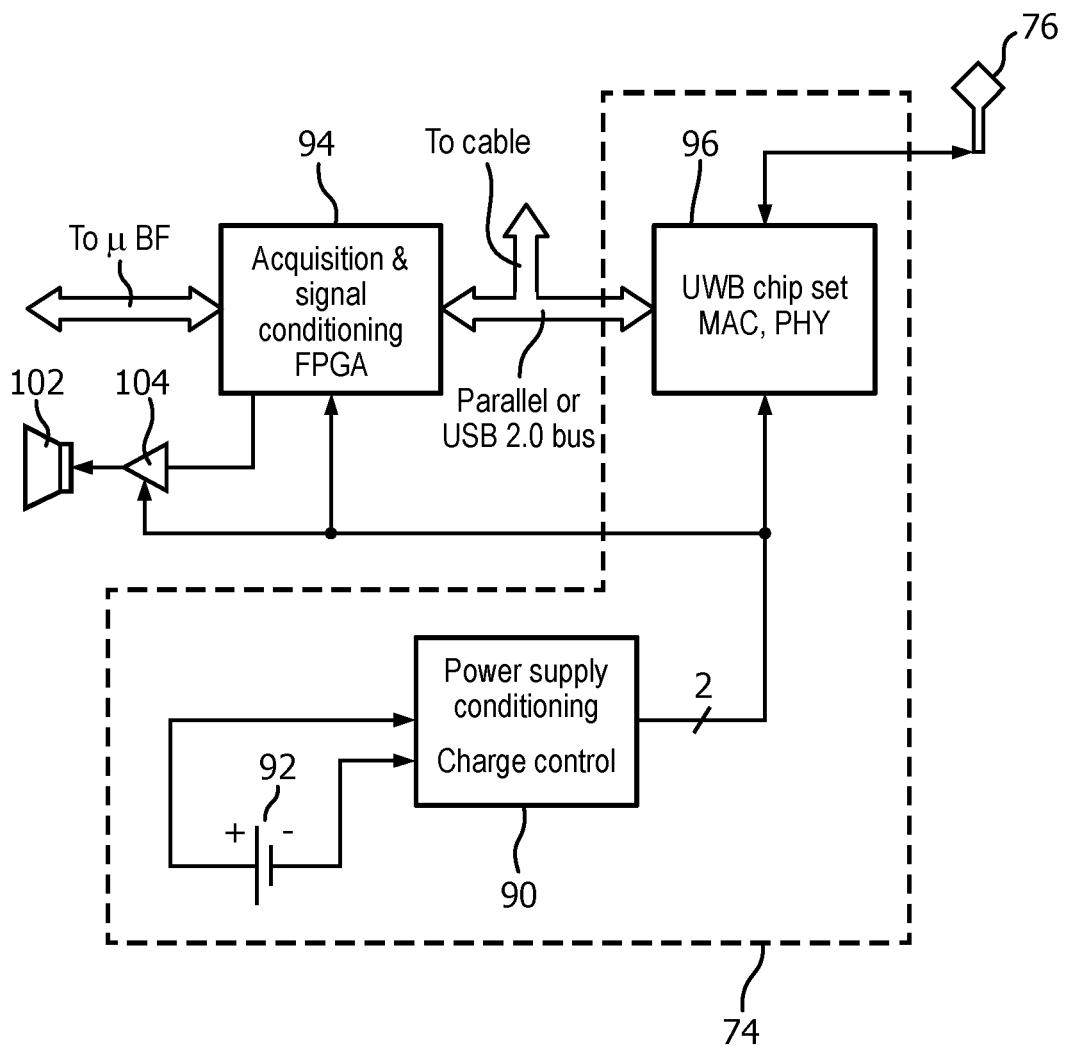
FIG. 5 illustrates in block diagram form the back end FPGA and ultra wideband chipset of the wireless ultrasound probe of FIG. 4.

A typical probe controller and transceiver subsystem for a wireless probe is shown in FIG. 5. A battery 92 powers the wireless probe and is coupled to a power supply and conditioning circuit 90. The power supply and conditioning circuit translates the battery voltage into a number of voltages required by the components of the wireless probe including the transducer array. A typical constructed probe may require nine different voltages, for example. The power supply and conditioning circuit also provides charge control during the recharging of the battery 92. In a constructed embodiment the battery is a lithium polymer battery which is prismatic and can be formed in a suitable shape for the available battery space inside the probe case.

An acquisition and signal conditioning FPGA 94 provides communication between the microbeamformer and the transceiver and performs signal conditioning as described below. The acquisition and signal conditioning FPGA provides timing and control signals to the microbeamformer in response to control parameters received from the processor dongle, directing the transmission of ultrasound waves and receiving beamformed echo signals from the microbeamformer, which are demodulated, detected and scan converted by the FPGA and communicated to the transceiver 96 for transmission to the host dongle. In this example the acquisition and signal conditioning FPGA communicates with the transceiver over a USB bus so that the probe can be used with a USB cable when desired. In the probe of FIG. 1(a) the USB bus is coupled to a detachable UWB radio power module. With a USB output, the probe can alternately be operated as a wired probe, with a USB cable of suitable length connecting the probe to the USB port of the dongle and dispensing with the radio module.

Also coupled to the acquisition and signal conditioning FPGA 94 and powered by the power supply and conditioning circuit 90 is a loudspeaker 102, driven by an amplifier 104, which produces audible tones or sounds. In a preferred embodiment the loudspeaker 102 is a piezoelectric loudspeaker located inside the probe case 8 and which may be behind a membrane or the wall of the case for good acoustics and sealing. The loudspeaker can be used to produce a variety of sounds or tones or even voice messages. The loudspeaker has a variety of uses. If the wireless probe is moved too far away from the host dongle so that there is unreliable reception or even a complete loss of signal by the dongle or the probe, the loudspeaker can beep to alert the user. The loudspeaker can beep when the battery charge is low. The loudspeaker can emit a tone when the user presses a button or control on the probe, providing audible feedback of control activation. The loudspeaker can provide haptic feedback based upon the ultrasound examination. The loudspeaker can emit a sound when a paging control is activated to locate the probe. The loudspeaker can produce audio Doppler sounds during a Doppler exam, or heart sounds when the probe is used as an audio stethoscope.

The transceiver radio in this example is an ultra wideband chip set 96, although it can also be a WiFi (802.11 standard) radio or other standard radio. An ultra wideband transceiver was found to have a data communication rate which provides acceptable real time imaging frame rates as well as acceptable range for an acceptable level of battery power consumption. Ultra wideband chip sets are available from a variety of sources such as Alereon of Austin, Tex. and Starix of Irvine, Calif. WiFi radio adapters such as the Netgear N300 wireless-N USB adapter are also suitable for wireless Wifi communication.

As previously mentioned, control of the ultrasound system can be provided by touch buttons on the touchscreen of a tablet computer 28, which is in wireless communication with the system. Alternatively, a wireless mouse can be used to manipulate a cursor over control buttons on the user display, clicking to select and change desired features. Wireless mouse pointers generally use Bluetooth communication and are wirelessly connected to the Bluetooth radio of a processor dongle such as the Intel compute stick. Yet another option is to use the wireless probe itself to control the user interface with gesture motions. FIGS. 6a, 6b and 6c illustrate a wireless probe equipped for gesture control of an ultrasound system of the present invention.

In the illustration of FIG. 6a, the acoustic window 12 of the probe 10 through which ultrasound waves are transmitted into the patient and echoes received in return is at the left, and a probe orientation marker 18 is on the bottom side of the probe in this view. Further details about the components of a wireless probe are found in U.S. Pat. No. 8,461,978 (Poland et al.) Inside the probe in this embodiment is a 3-axis or 6-axis motion sensor 14 such as an accelerometer. A probe containing such an accelerometer is described in U.S. Pat. No. 5,529,070 (Augustine et al.) In this patent the accelerometer is used to detect the position of the probe during three dimensional imaging. In the embodiment of FIG. 6a the accelerometer is used to sense probe motions for system control changes. The signals produced by the accelerometer are processed to produce indications of probe motion (acceleration, velocity, direction of motion, probe orientation) by a microcontroller in the wireless probe or by the acquisition and signal conditioning FPGA described above. Preferably the probe motions which are detected for user interface manipulation are ones which are distinct from motions commonly employed during scanning, such as spinning the probe. A wireless probe is ideally suited for such non-scanning probe motion as there is no cable to impede such motion. For instance, the user can readily spin the probe 10 180° around its long axis as indicated by arrow 36. This motion is sensed by the accelerometer, processed by the microcontroller or FPGA and communicated to the host dongle, which responds by switching the ultrasound system from the present scanning (imaging) mode to a control mode in which the user interface can be manipulated. This motion could also be done with a probe that utilizes a cable to connect to the display system. Preferably, however, the probe is a wireless probe 10 with a radio link replacing the cable to the system because the range of unimpeded motions available is broader with an un-cabled probe. In this wireless probe example, an example motion is to spin the probe 180 or 360 degrees in the palm of the hand as indicated by arrow 34. Once the system has been switched to the control mode, the probe is used as a remote user interface controller, wherein subsequent motions of the probe select and activate configuration parameters for scanning, such as the imaging mode (2D, Flow, CW, PW, etc.), the image Gain or Depth, or other system controls such as image review scrolling and capture and transfer of previously acquired still or cine loop images to storage. The system display will show the current and selectable configuration/control states of the system. On-screen menus, for instance, may be navigated by the motions of the probe while it is in control mode. Examples of probe motions which can be used to manipulate the system in the control mode are illustrated in FIG. 6c.

To return to the imaging mode, the user may employ the same probe motion so as to toggle the state of the system back to imaging, or use a motion in the reverse direction from the original. So in the example illustrated above, a second spin along the short (34) or long (36) axis of the probe can effect the switch, as indicated by the arrows. Alternatively, touching the probe to the skin surface of the patient to resume scanning can be used to return the probe and display system to the scanning mode. The detection of physical coupling of the probe 10 to the patient or the absence thereof has previously been used for energy conservation by an ultrasound system. When a probe is physically (acoustically) coupled to the patient, echoes from increasing depths are continually received following an ultrasound pulse transmission by the probe. But when the probe is returned to a probe holder or simply being held in the air, the only acoustic signal returned in response to a transmitted ultrasound pulse is the sharp reflection at the face of the lens due to the lens-air interface, and it is returned almost immediately after transmission. When the system senses that it is no longer receiving only signal returns from the face of the lens but is receiving signals from increasing depths (longer time) after pulse transmission, the system knows that the probe has returned to normal use for imaging and will toggle the system back to the imaging mode in response.

Other distinct motions to effect a mode change may alternatively be implemented, such as detecting a finger swipe on the surface of the probe using a capacitive sensor. Another possibility is to have a button on the probe that is used for mode switching. Neither of these approaches are preferred, however. The former requires another component in the probe, a capacitive sensor, and the placement of a button on the probe poses the difficulties described above (inadvertent actuation, fluid ingress, etc.)

FIG. 6b illustrates another implementation of probe motion control for an ultrasound system of the present invention. This illustration shows a probe 10 being held in the hand H of a sonographer. The probe 10 is shown held in a conventional scanning position, whereby the sonographer can press the acoustic window 12 of the probe into contact with the skin of a patient during scanning. In this example the distinct motion which is used to switch the ultrasound system to the control mode is to shake the probe up and down vigorously two or more times, as indicated by the arrow 38. This type of motion is one which is familiar to a sonographer, as it is the motion that a sonographer employs when shaking an acoustic coupling gel bottle to urge the gel in the bottle to the dispenser at the end of the bottle. While this is a familiar motion to a sonographer, it is not one used during imaging with the probe; it is one applied to a gel bottle in preparation for gel application for scanning. To switch from the imaging mode to the control mode, the sonographer simply lifts the probe 10 off of the patient and gives it two or more shakes 38. There is no need to alter the probe position in the hand H of the sonographer. The motion sensor in the probe 10 senses these quick motions and rapid reversals in the direction of probe movement and the FPGA 94 responds by changing the mode of the system to the control mode. When the sonographer lifts the probe away from contact with the patient, the only signal received in response to ultrasound pulse transmission are the reflections from the face of the acoustic window as described above, and this change in echo reception can be used to correlate with the probe motion as a confirmation that a system mode change is being commanded.

The display monitor 20 of FIG. 1(c) is shown displaying the ultrasound images produced by an implementation of the present invention in the center of the display screen. Details about the parameters of the scanning procedure such as imaging mode, frequency, focal depth, and the like are displayed to the right of the ultrasound image in this example. To the left of the ultrasound image are six displayed control buttons indicated at 24. When the system is switched to the control mode by any of the techniques described above, the cursor arrow to the right of the control buttons is moved up and down or around the screen in response to probe motion until the desired control is indicated by the cursor, and the control is then actuated by another probe motion. An example of these motions is shown in FIG. 6c. In this example the probe 10 is held with the acoustic window pointed upward, an orientation which is sensed by the motion sensor 14 inside the probe. The probe is then moved left, right, up or down as indicated by the arrows 40, with the arrow cursor on the tablet display moving across the screen in correspondence with these motions. Once the sonographer has positioned the arrow cursor over or pointing at the desired control, the sonographer rocks the end of the probe toward the display as indicated by the arrow 42. The rocking motion gives the sonographer the sense of touching or tapping the control with the end of the probe, even though the display is remote from the probe and the motion is only effected in the air. But the rocking motion is orthogonal to the cursor positioning motions 40, which are generally parallel to the plane of the display screen. Hence the control selection motion can be readily distinguished from the cursor manipulation motion, and the ultrasound system responds by actuating the selected control. Any of the imaging modes or control settings enumerated above can be selected and changed by this method of control. Once the controls have been set as desired for the scanning procedure, the system is returned to the scanning mode by one of the distinct motions described above (spinning the probe, shaking it rapidly) or by simply placing the acoustic window of the probe back into contact with the skin of the patient for imaging.

FIG. 7 illustrates the control of the ultrasound probe 10 by the Windows processor of a dongle 30 and the responsive image processing and other functions performed by the dongle. In a constructed implementation of the present invention the Windows 8 operating system of the dongle is running an ultrasound system control program found on a mid-range ultrasound system, in particular, the ultrasound control program of systems Sparq, CX50, and ClearVue, available from Philips. In FIG. 7 the control and operation of the FPGA 94 of the ultrasound probe is shown on the left side of the drawing. The Acquisition portion of the FPGA 94 accepts ultrasound probe control signals from the dongle ("Params") in the form of coefficients and uses them to configure the microbeamformer 72 for scanning. The Acquisition program uses the coefficients to start and stop scanning, to set transmit and receive delays for beamforming, and to set control voltages for ultrasound transmission. When the microbeamformer processes received echo signals they are coupled to the Acquisition portion which outputs them as acquired acoustic data.

The Signal Conditioning portion of the FPGA 94 receives the acoustic data from the Acquisition portion as a stream of data samples for each acoustic scan line. It processes them according to coefficients received from the Coefficient Generation block 58 of the dongle in accordance with the type of each scan line: grayscale, colorflow, PW Doppler, etc. The coefficients specify filter settings, gains, Doppler ensemble processing, PW mixing waveforms, and decimation size and bandwidth for each scan line. The Signal Conditioning portion of the FPGA produces fully detected grayscale, colorflow, continuous wave, and spectral Doppler data with signal amplitude and/or phase information needed by the Image Processing block 52 of the dongle to produce a rendered ultrasound image.

The Image Processing block 52 in the dongle accepts image line data from the probe and generates an ultrasound image for display on the receiver or monitor 20 to the user. Depending upon the display options selected by the user, block 52 can perform image persistence, axial and lateral filtering, scan conversion, image smoothing and enhancement, spatial compounding, thresholding, zoom, pan, harmonic image display, and zone focus zone stitching. Most of these operations are computationally intensive, particularly during control changes and live imaging, which is why they are executed by the Windows 8 OS in the dongle. Such computations often are image memory intensive and require working buffers, lending themselves well to computational performance in the dongle.

The Control block 56 receives commands from the user interface ("Cmd") and converts the commands into signals which define the next "State" of the system, that is, what the system is to do or image next. The State is reflected back to the user as "Feedback", confirming to the user that an issued command is being put into effect. The Coefficient Generation block 58 translates the State signals into specific coefficients for the probe hardware (Params) which implement the State of the system desired by the user. State signals are also coupled to and used by the Image Processing block 52 to produce an image of the desired type and format (sector, linear, grayscale, colorflow, etc.) commanded by the user.

The App Host 54 is a collection of conventional routines that the user expects to see in the user interface of an ultrasound system. Patient Data Entry (PDE)/Study manages the collection and reviewing of patient data and clinical studies for the ultrasound system. PDE/Study is responsible for accepting the input of patient data from the user as well as collecting any study data such as image loops or still images accumulated by the user during an exam. Main is the overall controller for all of the other component packages. Render performs the rendering of all image, graphic, and textual data into display signals for the display 20 in accordance with parameters provided by the Control block 56. Storage/Export manages the storage and retrieval of patient data and studies for the system and on local, removable, or remote media used with the system. Other functions installed on the system are included in Other Apps.

FIG. 8 is a flowchart of the operation of the ultrasound system of FIGS. 2 and 7, starting with the connection of a Windows processor dongle 30 to a display 20 and the powering up of a probe. Shown in brackets in each step is the block or portion of FIG. 7 which is carrying out a given operation. "UI" is a block responsible for generating the on-screen display elements (see FIG. 3) that the user can interact with to change system state, such as buttons, scroll wheels, etc., and is also responsible for responding to user interface commands issued by the user by means of the system user interface, such as probe gestures, mouse, touchscreen, hard controls, etc. The steps carried out by the probe 10 are in the sequence on the left side of the drawing under the heading "Probe," and the steps carried out by the processor dongle 30 are in the sequence on the right side of the drawing under the heading "Host." Communication between the probe and the processor dongle is indicated by the dashed arrows between the two sequences.

Initially at 60 in this example the probe is turned off. The host dongle is turned on and connected to the display at 110 as shown in FIG. 2. The dongle repeats checks at 112 to see whether the probe is in communication with it. When the probe is turned on at 62, it repeatedly checks at 64 to see whether it is connected to the host and if the host is available, it automatically connects with the host if previously paired, or goes through its pairing protocol if not, as described in application U.S. Prov. Appl. No. 62/193,210, entitled "WIRELESS ULTRASOUND PROBE PAIRING WITH A MOBILE ULTRASOUND SYSTEM" (Bell et al.), which is incorporated by reference herein, as indicated by the first dashed arrow. With communication established the user selects the desired preset, the imaging mode (e.g., grayscale), and control states from the user interface at 114. At 116 the host converts the selected state of the system to imaging control parameters. The parameters are used at 118 to generate beamforming, demodulation, and scanning coefficients for the probe, and at 120 the coefficients are downloaded to the Signal Conditioning portion of the probe. The coefficients are received by the probe at 66 and stored in memory and used to define probe's transmit and receive operation for image acquisition, such as the size and depth of the scanning area, focal zones, beam steering, bandwidth, harmonic or fundamental mode, ensemble length for Doppler, etc. At 68 the probe checks to see whether scanning is active. If so, the stored coefficients are used to set up the microbeamformer for the desired scanning and beams are transmitted and scan lines of echoes are received at 80. The received raw acoustic echo signals are demodulated and detected at 82. Transmission and reception continues until a full image frame has been received at 84. When a frame has been received and processed into lines of display data, the frame lines are sent to the host dongle at 86, and the probe continues to acquire further frames.

In the host dongle, the host is periodically checking at 122 to see if any of the image control parameters have changed. If they have, the dongle stops scanning at 128 and uses the new user control settings at 114 to establish a new imaging state. If there has been no change in the image control parameters, the host checks at 124 to see if the freeze control has been activated to freeze the current image on the display. If freeze has been activated, the host stops scanning at 126 and continues to check at 122 for any change in the image control settings. If freeze has not been activated, scanning is stopped at 130 and the host receives a new frame of scan line data from the probe at 132. The new frame is processed in the host at 134 as commanded by the user to apply gain, splice partial zone focus scan lines, perform data compression, etc., as described in conjunction with FIG. 7. The processed image frame data is scan converted at 136 into the desired image format (sector, linear, 3D, etc.) and the frame is rendered into an image for display on the display receiver or monitor. The process then goes back to step 122 to await the next image frame or a change in the image control settings.

The above operational example is generalized to illustrate system performance for basic grayscale imaging. Variations to accommodate colorflow, PW Doppler, CW Doppler, harmonic, and/or 3D modes will be readily apparent to those skilled in the art.

It should be noted that the various embodiments described above and illustrated by the exemplary ultrasound system described herein may be implemented in hardware, software or a combination thereof. The various embodiments and/or components, for example, the modules, or components and controllers therein, also may be implemented as part of one or more computers or microprocessors. The computer or processor may include a computing device, an input device, a display unit and an interface, for example, for accessing the Internet. The computer or processor may include a microprocessor. The microprocessor may be connected to a communication bus, for example, to access a PACS system. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, solid-state thumb drive, and the like. The storage device may also be other similar means for loading computer programs or other instructions into the computer or processor.

As used herein, the term "computer" or "module" or "processor" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of these terms.

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

Furthermore, the limitations of the following claims are not written in means-plus-function format and are not intended to be interpreted based on 35 U.S.C. 112, sixth paragraph, unless and until such claim limitations expressly use the phrase "means for" followed by a statement of function devoid of further structure.

What is claimed is:

1. An ultrasound system comprising:
    a wireless ultrasound probe comprising a radio and configured to receive ultrasound probe control signals and send ultrasound image scan line data based on the control signals;
    a processor dongle having a digital processor configured to run an operating system and an ultrasound system control program and a radio, the dongle being configured to receive user interface commands for an imaging procedure, send ultrasound probe control signals to the ultrasound probe, receive image line data signals from the probe, and perform image processing of received image line data signals to generate an ultrasound image for display; and
    a display coupled to the processor dongle and configured to display the ultrasound image generated by the dongle.

2. The ultrasound system of claim 1, wherein the processor dongle further comprises an HDMI connector that is removably coupled to an HDMI port of the display.

3. The ultrasound system of claim 1, wherein the radios each comprise an ultra-wideband (UWB) radio and the processor dongle further comprises an input port; and the system further comprises a UWB dongle plugged into the input port.

4. The ultrasound system of claim 1, wherein the radio in the processor dongle comprises a Wifi radio;
    wherein the display comprises a television receiver or display monitor further comprising a Wifi radio; and
    wherein the display is coupled to the processor dongle using the Wifi radios.

5. The ultrasound system of claim 1, further comprising:
    an a.c. adapter configured to connect to and power the processor dongle when plugged into an a.c. outlet;
    wherein the processor dongle further comprises a port configured to connect a cable to the wireless probe for data transfer comprising the image line data signals;
    wherein the display further comprises a radio and the display is configured to couple to the processor dongle using the radio.

6. The ultrasound system of claim 1, wherein the display further comprises a patient monitor.

7. The ultrasound system of claim 1, further comprising a tablet computer having a Wifi radio;
    wherein the processor dongle radio further comprises a Wifi radio;
    wherein the tablet computer displays the ultrasound image generated by the dongle.

8. The ultrasound system of claim 7, wherein the tablet computer further displays user interface controls which are operated by a user to control the ultrasound system.

9. The ultrasound system of claim 1, wherein the ultrasound probe further comprises a motion sensor which generates signals in response to probe motion;
    wherein the processor dongle is responsive to signals generated in response to probe motion to control the operation of the ultrasound system.

10. An ultrasound system comprising:
    an ultrasound probe having a probe cable configured to receive ultrasound probe control signals and send ultrasound image scan line data based on the control signals;
    a processor dongle having a port to which the probe cable is connected and a digital processor configured to run an operating system and an ultrasound system control program, the dongle being configured to receive user interface commands for an imaging procedure, send ultrasound probe control signals to the ultrasound probe, receive image line data signals from the probe, and perform image processing of received image line data signals to generate an ultrasound image for display; and
    a display coupled to the processor dongle and configured to display the ultrasound image generated by the dongle.

11. The ultrasound system of claim 10, wherein the processor dongle further comprises a radio;
    wherein the display further comprises a radio; and
    wherein the display is coupled to the processor dongle by the radio.

12. The ultrasound system of claim 10, wherein the processor dongle further comprises a connector;
    wherein the display further comprises a data port;
    wherein the processor dongle connector is coupled to the data port.

* * * * *